United States Patent
Li et al.

(10) Patent No.: US 12,133,771 B2
(45) Date of Patent: Nov. 5, 2024

(54) COMBINED FREQUENCY AND ANGLE COMPOUNDING FOR SPECKLE REDUCTION IN ULTRASOUND IMAGING

(71) Applicants: The Board of Trustees of the Leland Stanford Junior University, Stanford, CA (US); THORLABS, INC., Newton, NJ (US)

(72) Inventors: Yilei Li, Stanford, CA (US); Steven Chu, Stanford, CA (US); Noah Yuzo Toyonaga, Stanford, CA (US); James Y Jiang, Newton, NJ (US); Alex E. Cable, Newton, NJ (US)

(73) Assignees: The Board of Trustees of the Leland Stanford Junior University, Stanford, CA (US); THORLABS, INC., Newton, NJ (US)

( * ) Notice: Subject to any disclaimer, the term of this patent is extended or adjusted under 35 U.S.C. 154(b) by 56 days.

(21) Appl. No.: 17/257,251

(22) PCT Filed: May 21, 2019

(86) PCT No.: PCT/US2019/033272
§ 371 (c)(1),
(2) Date: Dec. 30, 2020

(87) PCT Pub. No.: WO2019/226626
PCT Pub. Date: Nov. 28, 2019

(65) Prior Publication Data
US 2021/0212668 A1    Jul. 15, 2021

Related U.S. Application Data

(60) Provisional application No. 62/675,032, filed on May 22, 2018.

(51) Int. Cl.
*A61B 8/00*    (2006.01)
*A61B 8/08*    (2006.01)
(Continued)

(52) U.S. Cl.
CPC .......... *A61B 8/5269* (2013.01); *A61B 8/4218* (2013.01); *A61B 8/4254* (2013.01);
(Continued)

(58) Field of Classification Search
CPC ... A61B 8/5253; A61B 8/5269; A61B 8/4218; A61B 8/4254; A61B 8/4263;
(Continued)

(56) References Cited

U.S. PATENT DOCUMENTS 6,126,599 A    10/2000   Jago et al.
6,283,917 B1 *   9/2001   Jago .................... G01S 15/8995
                                                               600/443
(Continued)

FOREIGN PATENT DOCUMENTS

WO    WO-2017182397 A1 * 10/2017 ........... A61B 8/0825

OTHER PUBLICATIONS

European Patent Application No. 19807129.2, Extended European Search Report, Jan. 11, 2022, 10 pages.
(Continued)

*Primary Examiner* — Joel Lamprecht
(74) *Attorney, Agent, or Firm* — Kilpatrick Townsend & Stockton LLP

(57) ABSTRACT

This disclosure relates to combined frequency and angle compounding for speckle reduction in ultrasound imaging. Such combined frequency and angle compounding can result in a multiplicative speckle reduction compared to using either frequency compounding or angle compounding alone. Compounding methods of this disclosure can make use of the full aperture of the ultrasound probe when (Continued)

acquiring individual images, hence there can be no compromise in resolution. In disclosed embodiments, ultrasound images can be obtained while an ultrasound probe is moving and the relative position and orientation of the ultrasound images can be determined from a measurement of the position and orientation of the ultrasound probe. Certain embodiments can correct for the movement and distortion of an object being imaged during the image acquisition.

26 Claims, 15 Drawing Sheets

(51) Int. Cl.
    *G01S 15/89*     (2006.01)
    *G01S 17/66*     (2006.01)

(52) U.S. Cl.
    CPC .......... *A61B 8/4263* (2013.01); *A61B 8/4488* (2013.01); *A61B 8/463* (2013.01); *A61B 8/5253* (2013.01); *G01S 15/8915* (2013.01); *G01S 15/8952* (2013.01); *G01S 15/8995* (2013.01); *G01S 17/66* (2013.01); *A61B 2562/0219* (2013.01); *A61B 2562/0247* (2013.01)

(58) Field of Classification Search
    CPC ................. A61B 8/4488; A61B 8/463; A61B 2562/0219; A61B 2562/0247; A61B 8/4245; G01S 15/8995; G01S 15/8915; G01S 15/8952; G01S 17/66; G01S 15/8936
    See application file for complete search history.

(56) References Cited

U.S. PATENT DOCUMENTS

| | | | | |
|---|---|---|---|---|
| 6,390,981 | B1* | 5/2002 | Jago | G01S 15/892 |
| | | | | 600/443 |
| 6,511,426 | B1 | 1/2003 | Hossack et al. | |
| 7,338,448 | B2* | 3/2008 | Hao | G01S 15/8995 |
| | | | | 600/443 |
| 8,068,647 | B2* | 11/2011 | Lin | G03B 42/06 |
| | | | | 382/128 |
| 9,561,019 | B2* | 2/2017 | Mihailescu | A61B 8/4438 |
| 2004/0243001 | A1* | 12/2004 | Zagzebski | G01S 15/8995 |
| | | | | 600/437 |
| 2005/0101865 | A1* | 5/2005 | Hao | G01S 7/52038 |
| | | | | 600/447 |
| 2007/0014445 | A1* | 1/2007 | Lin | G03B 42/06 |
| | | | | 382/128 |
| 2008/0188751 | A1* | 8/2008 | Sato | G01S 15/8981 |
| | | | | 600/454 |
| 2008/0208061 | A1* | 8/2008 | Halmann | G01S 15/8995 |
| | | | | 600/459 |
| 2013/0237811 | A1* | 9/2013 | Mihailescu | A61B 8/4245 |
| | | | | 600/407 |
| 2013/0258805 | A1* | 10/2013 | Hansen | G01S 7/52046 |
| | | | | 367/8 |
| 2014/0066768 | A1* | 3/2014 | Sui | G01S 15/8915 |
| | | | | 600/443 |
| 2015/0130901 | A1* | 5/2015 | Sornes | G06T 7/246 |
| | | | | 348/46 |
| 2015/0293222 | A1* | 10/2015 | Huang | G01S 15/8977 |
| | | | | 367/87 |
| 2016/0140738 | A1* | 5/2016 | Asaka | G01S 15/8952 |
| | | | | 382/131 |
| 2017/0252007 | A1* | 9/2017 | Mine | A61B 8/4218 |

OTHER PUBLICATIONS

Hansen, C. et al., Three-dimensional Reconstruction of Fine Vascularity in Ultrasound Breast Imaging Using Contrast-enhanced Spatial Compounding: In Vitro Analyses, Academic Radiology, 15(9):1155-1164, Sep. 2008.
International Patent Application No. PCT/US2019/033272, International Search Report and Written Opinion of the International Searching Authority, Aug. 2, 2019, 11 Pages.
Macione, J. et al., "Paired-Angle Multiplicative Compounding," Ultrasonic Imaging, 30(2):112-130, Apr. 2008.
Tsubai, M. et al., "A Portable Measuring System for Cross-Sectional Ultrasound Images Using Spatial Compounding and Edge Sharpening," Proceedings of the 29th Annual International Conference of the IEEE EMBS, Cité Internationale, Lyon, France, Aug. 23-26, 2007, pp. 2150-2154.
AU2019274464, First Examination Report, Mar. 30, 2022, 4 pages.
Li, et al., Multiplicative Frequency and Angular Speckle Reduction in Ultrasound Imaging, bioRxiv 2023-10-26.564267; doi: https://doi.org/10.1101/2023.10.26.564267.
Lorenz, et al., A Gaussian Model Approach for the Prediction of Speckle Reduction with Spatial and Frequency Compounding, 1996 IEEE Ultrasonics Symposium, 1996, pp. 1097-1101, 0-7803-3615-1/96.
Trahey et al., A Quantitative Approach to Speckle Reduction via Frequency Compounding, Ultrasonic Imaging 8, 1986, pp. 151-164, Academic Press, Inc.

\* cited by examiner

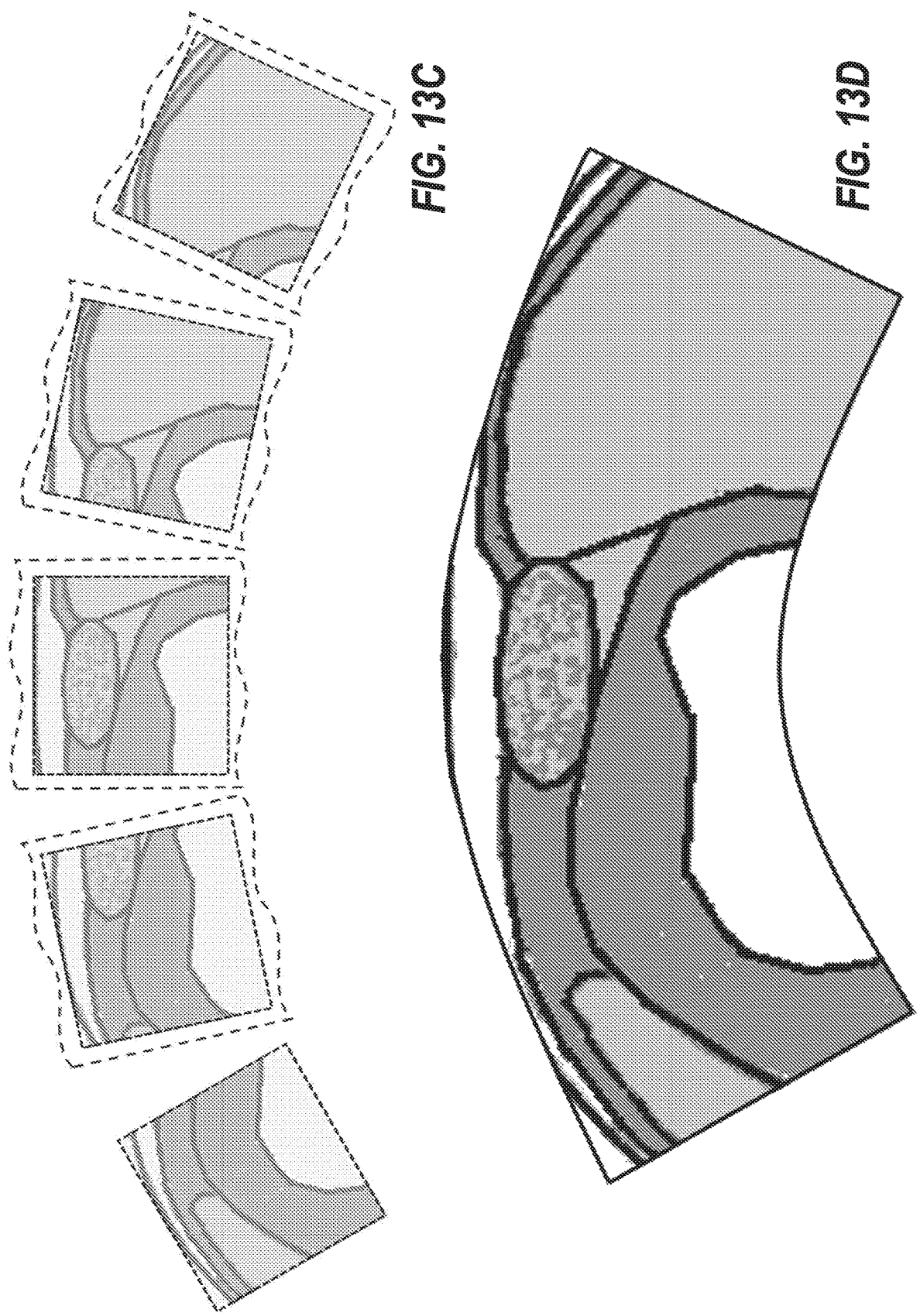

COMBINED FREQUENCY AND ANGLE COMPOUNDING FOR SPECKLE REDUCTION IN ULTRASOUND IMAGING

RELATED APPLICATION

The present application is a national phase application under 35 U.S.C. 371 claiming priority to PCT/US2019/033272, filed May 21, 2019, which application claims the benefit of priority of U.S. Provisional Patent Application No. 62/675,032, filed May 22, 2018, titled "COMBINED FREQUENCY AND ANGLE COMPOUNDING FOR SPECKLE REDUCTION IN ULTRASOUND IMAGING," the disclosures of which are hereby incorporated by reference herein in their entirety for all purposes.

BACKGROUND

Technological Field

The disclosed technology relates to ultrasound imaging.

Description of the Related Technology

Ultrasound is becoming an increasingly important tool for diagnostic imaging with many desirable characteristics. Ultrasound is relatively fast, real-time imaging, at low cost, and without exposure to ionizing radiation. In addition, refinements such as color Doppler, shear wave and contrast agent labeling offer valuable additional diagnostic information that can complements x-ray, computed tomography (CT) and magnetic resonance imaging (MRI) imaging modalities. However, conventional ultrasound imaging suffers from the presence of significant speckle noise, and useful resolution of ultrasound imaging in clinical practice is degraded.

SUMMARY OF CERTAIN ASPECTS

The innovations described in the claims each have several aspects, no single one of which is solely responsible for its desirable attributes. Without limiting the scope of the claims, some prominent features of this disclosure will now be briefly described.

One aspect of this disclosure is a method of generating an ultrasound image with reduced speckle. The method comprises positioning an ultrasound probe at a first position and angle with respect to an object being imaged; applying, with the ultrasound probe at the first position and angle, multiple ultrasound frequencies in a first transmitting ultrasound beam directed at the object; receiving first ultrasound echoes from the object corresponding to the first transmitting ultrasound beam; generating first image data of a voxel of the object that corresponds to the received first ultrasound echoes; positioning the ultrasound probe at a second position and angle with respect to an object being imaged; applying, with the ultrasound probe at the second position and angle, multiple ultrasound frequencies in a second transmitting ultrasound beam directed at the object; receiving second ultrasound echoes from the object corresponding to the second transmitting ultrasound beam; generating second image data of the voxel of the object that corresponds to the received second ultrasound echoes; aligning, with a processing circuit, the first image data and the second image data; compensating for tissue distortion in the aligned first and second image data; frequency compounding and angle compounding the first and second image data so as to generate compounded data for the voxel, wherein the aligning and compensating are performed prior to at least the angle compounding; and outputting an ultrasound image corresponding to at least the voxel.

Another aspect of this disclosure is a method of generating an ultrasound image with reduced speckle. The method comprises generating, using an ultrasound probe, first image data for a voxel of an object corresponding to a first angle and multiple frequencies of the ultrasound probe; generating, using the ultrasound probe, second image data for the voxel of the object corresponding to a second angle and multiple frequencies of the ultrasound probe, wherein the first image data and the second image data correspond to the same voxel imaged from different angles; frequency compounding and angle compounding the first and second image data to generate at least a portion of an ultrasound image that corresponds to the voxel; and outputting the ultrasound image.

The angle (spatial) compounding process can include compounding images in the same plane of imaging. The multiple frequencies of the ultrasound probe for the first image data can be the same as the multiple frequencies of the ultrasound probe for the second image data.

Generating the ultrasound image data can use substantially a full aperture of the ultrasound probe.

Angle (spatial) compounding the ultrasound image data can comprise averaging and/or multiplying a first ultrasound image associated with the first position and a second ultrasound image associated with the second position.

The method can include moving the ultrasound probe from a first position corresponding to the first angle to a second position corresponding to the second angle. The method can include determining an amount (e.g., in terms of position and/or orientation) by which the ultrasound probe moves from the first position to the second position using an inertial sensor. Moving the ultrasound probe can include using a robot arm in some instances. An optical system, such as an optical coherence tomography system, can detect an amount by which the ultrasound probe moves from the first position to the second position in some instances.

The method can include detecting the first position and the second position, in which the ultrasound image data is generated based on the detected positions. The positions can be detected using an optical system. The positions can be detected based on tracking a movement of a robot arm. The positions can be detected based on an inertial sensing device.

The method can include aligning a first image data and the second image data, in which the angle compounding is based on the aligned first and second image data. Aligning can include rotating and translating at least one of the first image or the second image.

The method can include applying tissue distortion compensation to the ultrasound image data, in which the tissue distortion is obtained by comparing at least two aligned images and elastically distorting the second image to match the first image. The tissue distortion compensation can be combined with an image registration algorithm.

Generating the ultrasound data can include processing an echo to generate ultrasound images for the multiple of frequencies. Generating the ultrasound data can include transmitting ultrasound signals having different frequencies using the ultrasound probe. Alternatively, a single pulse with a relatively wide frequency spectrum can be used, and the received echo signal can be Fourier-filtered into several different frequency bands. Independent speckled images formed for the frequency bands can then be frequency compounded. The effective bandwidth of the transducer can be extended by compensating the natural response with a transmitting power spectrum that places more radio frequency (RF) power in the wings of the frequency response of the transducer.

The method can include sensing pressure applied by the ultrasound probe to an object corresponding to the ultrasound image data.

The method can include visually displaying the ultrasound image on a display. False color display can be used to help a clinician or other user observe finer shades of gray in the contrast. In some instances, the method can include visually displaying information to a guide an operator of the ultrasound probe regarding movement of the ultrasound probe.

The method can include frequency compounding and angle compounding third and fourth image data to generate another portion of the ultrasound image that corresponds to a second voxel. Overlap of the third and fourth image data can correspond to only a portion of the second voxel being imaged from different angles.

Another aspect of this disclosure is an ultrasound imaging system for generating an ultrasound image with reduced speckle. The ultrasound imaging system includes an ultrasound probe and a processing circuit. The ultrasound probe is configured to transmit ultrasound signals and receive echoes of the ultrasound signals. The ultrasound probe is arranged to obtain echo data for the same voxel from at a plurality of different angles. The processing circuit is in communication with the ultrasound probe. The processing circuit is configured to receive echo data for the voxel corresponding to at least two different angles of the plurality of angles, in which the echo data corresponding to multiple frequencies for each of the at least two different angles. The processing circuit is configured to align the echo data for the voxel corresponding to at least two different angles of the plurality of angles. The processing circuit is configured to frequency compound and angle compound the echo data to generate compounded ultrasound image data, in which the processing circuit is configured to angle compound the echo data after the echo data is aligned. The processing circuit is configured to output an ultrasound image based on the compounded ultrasound image data.

The ultrasound imaging system can include a robot arm configured to move the ultrasound probe between the different positions. The processing circuit can detect the probe positions based on movement of the robot arm.

The ultrasound imaging system can include an optical system, in which the processing circuit is configured to detect probe positions based on an output of the optical system. The ultrasound imaging system can include an inertial sensor, in which the processing circuit is configured to detect movement of the ultrasound probe between different positions corresponding to the plurality of different angles based on output data from the inertial sensor. The processing circuit can be configured to align the first echo data and the second echo data based on the detected movement.

The ultrasound imaging system can include a light detection and ranging (LIDAR) based sensor. The processing circuit can be configured to detect movement of the ultrasound probe between different positions corresponding to the plurality of different angles based on output data from the LIDAR based sensor. The processing circuit can be configured to align the first echo data and the second echo data based on the detected movement.

The processing circuit can perform angle compounding by at least averaging and/or multiplying corresponding pixels in the ultrasound image data associated with the two different positions.

The processing circuit can apply a tissue distortion compensation operation to the ultrasound image data.

The ultrasound imaging system can include a pressure sensor integrated with the ultrasound probe.

The ultrasound imaging system can include a display configured to visually display the ultrasound image.

The compounded ultrasound image data can represent a B-mode image. The image can include a 2D array of pixels representing an area or a 3D array of pixels representing a volume.

Another aspect of this disclosure is a method of generating ultrasound image with reduced speckle. The method includes generating, using an ultrasound probe in a first position, first image data for a voxel corresponding to multiple frequencies; moving the ultrasound probe from the first position to a second position; tracking the motion of the ultrasound probe during the moving so as to generate movement data; generating, using the ultrasound probe in the second position, image data for the voxel corresponding to multiple frequencies, wherein the first image data and the second image data correspond to the same voxel imaged from different angles; aligning, with a processing circuit, the first image data and the second image data based on the movement data; frequency compounding and angle compounding the first and second image data so as to generate compounded data for the voxel, wherein the aligning is performed prior to angle compounding; and outputting an ultrasound image corresponding to at least the voxel, wherein the ultrasound image has a resolution that corresponds to substantially a full aperture of the ultrasound probe.

For purposes of summarizing the disclosure, certain aspects, advantages and novel features of the innovations have been described herein. It is to be understood that not necessarily all such advantages may be achieved in accordance with any particular embodiment. Thus, the innovations may be embodied or carried out in a manner that achieves or optimizes one advantage or group of advantages as taught herein without necessarily achieving other advantages as may be taught or suggested herein.

BRIEF DESCRIPTION OF THE DRAWINGS

Embodiments of this disclosure will now be described, by way of non-limiting examples, with reference to the accompanying drawings.

FIGS. 13A, 13B, 13C, and 13D illustrate images generated using the ultrasound probe of FIG. 12 and further processing by the processing circuit according to an embodiment.

DETAILED DESCRIPTION OF CERTAIN EMBODIMENTS

Figure 1:
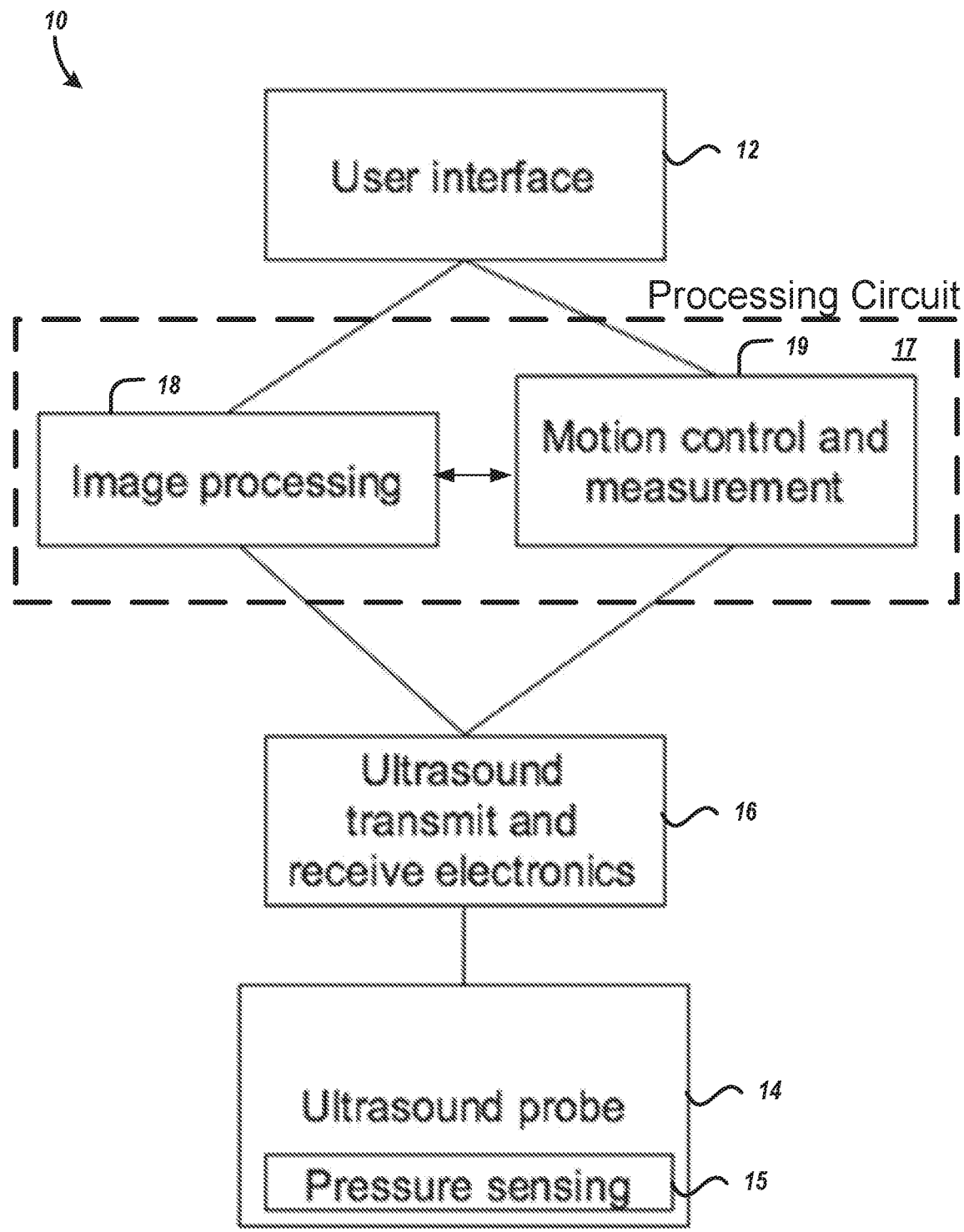
FIG. 1 is a block diagram of an ultrasound system with combined frequency and angle compounding according to an embodiment.

The following detailed description of certain embodiments presents various descriptions of specific embodiments. However, the innovations described herein can be embodied in a multitude of different ways, for example, as defined and covered by the claims. In this description, reference is made to the drawings where like reference numerals can indicate identical or functionally similar elements. It will be understood that elements illustrated in the figures are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings.

Ultrasounds are sound waves with frequencies above the audible range of humans. Ultrasound frequencies are typically in a range above 20 kilohertz (kHz) up to several gigahertz (GHz). As discussed above, conventional ultrasound imaging can experience significant speckle noise.

Speckle noise can result from coherent back-scattering of sound by the distribution of scatterers within each scattering voxel. In each voxel, suppose we have scattering amplitudes $A_1(\vec{x_1})$, $A_2(\vec{x_2})$, $A_3(\vec{x_3})$, .... If these amplitudes interfere constructively or destructively, the scattered signal $|A_1(\vec{x_1})+A_2(\vec{x_2})+A_3(\vec{x_3})+\ldots|^2$ can be either more or less than the sum of the scattering intensities of each of the scatterers, $|A_1(\vec{x_1})|^2+|A_2(\vec{x_2})|^2+|A_3(\vec{x_3})|^2+\ldots$, thus producing speckle.

Speckle can be reduced by up to $\sqrt{N}$ by averaging N speckle images, in which N is a positive integer. The upper limit can be achieved when the speckle in the N images are completely independent. The speckle images can be obtained by varying the frequency of sound (frequency compounding) or by varying the angle of incidence (angle compounding). Variations in frequency and/or angle can change the relative phase among the scatterers, and hence can change the speckle pattern. Angle compounding has been previously implemented using portions of an ultrasound array to produce images of a region from different angles. In a linear array of total aperture length L, the transverse resolution at any given depth z is approximately proportional to L/z. If the aperture is broken into N sub-segments, the spatial aperture of each view is decreased by N and the transverse resolution becomes (L/N)/z, N times worse than using the full aperture. Angle compounding is also known as spatial compounding. Using transform limited pulses is a method to optimize frequency compounding to reduce speckle.

This disclosure provides combined frequency and angle compounding methods that achieve a multiplicative speckle reduction as compared to that of either frequency or angle compounding alone. Averaging speckle images from M angles and N frequencies at each angle can reduce speckle by up to $\sqrt{MN}$. The multiplicative reduction in speckle can originate from the independence in the speckle variations with frequency and angle. Using such a method, a speckle reduction of more than 10-fold can be achieved.

Compounding speckle images with different angles of incidence can be referred to as spatial compounding, referring to the fact that the imaging aperture are at different spatial locations when the angle of incidence is changed. The term "angle compounding" is used herein to emphasize that speckle can be a function of the angle of incidence.

Angle (spatial) compounding processes discussed herein include compounding images in the same plane of imaging. These angle compounding processes are different from generating a compounded image that is an average of images obtained from several different, closely located scan planes. Angle compounding processes disclosed herein can image the same voxel from different angles. This is different than imaging adjacent voxels and averaging. By imaging the same voxel from different angles, an ultrasound image may not sacrifice resolution.

An angle compounding method described herein makes use of the full aperture of the ultrasound probe when acquiring individual images. Hence, there can be no compromise in resolution. Angle compounding methods disclosed herein can make use of substantially the full aperture of the ultrasound probe. Substantially the full aperture of the ultrasound probe can be at least 90% of the full aperture of the ultrasound probe, at least 95% of the full aperture of the ultrasound probe, at least 98% of the full aperture of the ultrasound probe, or the full aperture of the ultrasound probe.

The probe can be tracked using a robot arm, a free-space optical coherence tomography device, an inertial sensor, a light detecting and ranging (LIDAR) system, or any other suitable method. A combined image registration and elastic image registration algorithm can be used to angle compound images in certain embodiments. Any other suitable method to register the images taken from different angles can alternatively be used. By multiplying the images taken from different angles, the resolution can surpass the better resolution of the transverse and axial resolutions. Precise measurement of the ultrasound probe position and orientation can provide an initial alignment of the images.

FIG. 1 is a block diagram of an ultrasound system 10 with combined frequency and angle compounding according to an embodiment. As illustrated, the ultrasound system 10 includes a user interface 12, an ultrasound probe 14, a pressure sensor 15, ultrasound transmit and receive electronics 16, and a processing circuit 17. The illustrated processing circuit 17 includes an image processor 18 and a motion control and measurement circuit 19. The ultrasound system 10 can perform combined angle and frequency compounding on an ultrasound image and output a compounded ultrasound image with reduced speckle. In particular, the image processor 18 can perform combined frequency and angle compounding on ultrasound image data generated using the ultrasound probe 14.

The user interface 12 can display the current frame ultrasound image and/or a compounded ultrasound image. The user interface 12 can allow an operator to define one or more of the imaging parameters, such as the region of interest (ROI) and/or imaging angles and/or frequencies for frequency compounding.

The ultrasound probe 14 can be any suitable probe to transmit ultrasound signals and receive echoes of the transmitted ultrasound signals. The ultrasound probe 14 can include one or more ultrasound transducers. The ultrasound probe 14 can be moved by the operator directly and/or indirectly. As one example, the ultrasound probe 14 can be moved by a robot arm controlled by the operator. The position and orientation of the ultrasound probe 14 can be continuously and/or periodically measured while the ultrasound probe 14 is moving. Acoustic coupling between a transducer of the ultrasound probe 14 and a patient or other subject can be achieved with acoustic gel or water.

The pressure sensor 15 can be integrated with the ultrasound transducer 14. The pressure sensor 15 can detect an amount of pressure that the ultrasound probe 14 applies to a subject. Data from the pressure sensor 15 can be used in tissue distortion compensation by the image processor 18. The pressure sensor 15 can provide an indication that the ultrasound probe 14 is applying more than a threshold of pressure to a subject.

The ultrasound system 10 can acquire ultrasounds images, such as B-mode ultrasound images. The ultrasound images can be acquired continuously, periodically, intermittently, in response to an event (e.g., triggering by an operator), or any suitable combination thereof. The ultrasound transmit and receive electronics 16 can cause the ultrasound probe 14 to transmit pulses with desired center frequencies and bandwidths. The echoes of the transmitted ultrasound pulses can be received by the ultrasound probe 14 and processed by the transmit and receive electronics 16. Accordingly, real-time ultrasound images can be generated by the ultrasound system 10.

The image processor 18 of the processing circuit 17 can perform frequency compounding. Frequency compounding can be performed based on the ultrasound receive electronics performing Fourier filtering and/or based on the ultrasound probe 14 transmitting the frequencies separately. The bandwidth of the transducer of the ultrasound probe 14 can be extended by using a transmission power spectrum that compensates for the natural frequency response of the transducer. Images that include the ROI at the desired angles can be used for angle compounding by the image processor 18. The image processor can use information provided by one or more other images to register the images and/or correct for distortions in tissue of a subject being imaged. The image processor 18 of the processing circuit 17 can also perform angle compounding in accordance with any suitable principles and advantages disclosed herein.

The image processor 18 can perform image registration. The motion control and measurement circuit 19 can measure movement of the ultrasound probe 14. The motion control and measurement circuit 19 can generate movement data indicative of position and/or orientation of the ultrasound probe 14. Initial image registration can be performed by rotating and/or translating the individual images considering the measured movement of the ultrasound probe 14. Fine tuning of the image registration can be performed by calculating the correlation in consecutive images for one or more of translation, rotation, or elastic deformation. Optimized image registration can be achieved when the correlation is maximized.

Figure 2:
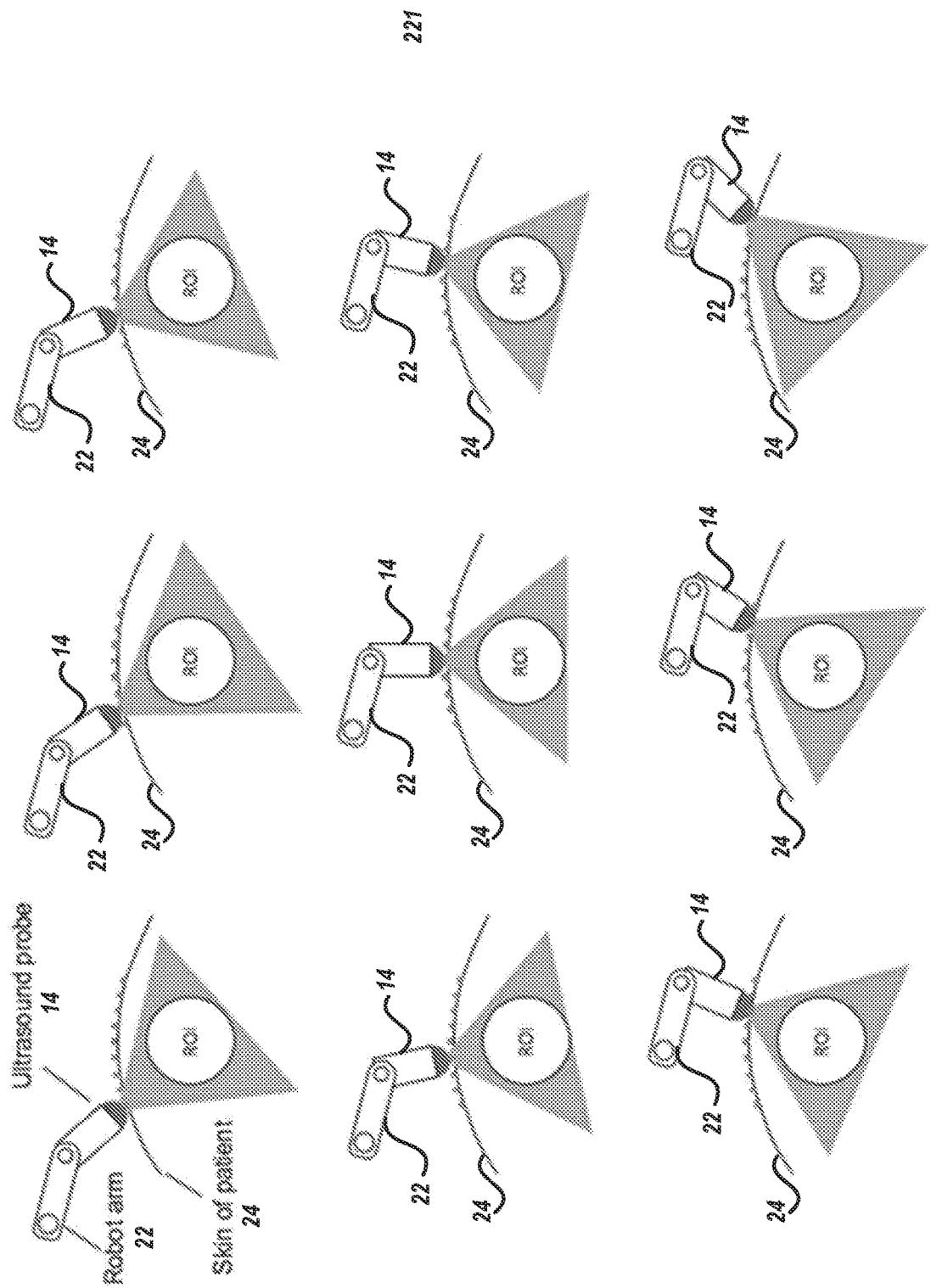
FIG. 2 illustrates an ultrasound system with an ultrasound probe moved by a robot arm to several different positions according to an embodiment.

In one embodiment, as illustrated in FIG. 2, the ultrasound probe 14 is attached to a robot arm 22. The robot arm 22 can be either active with joints powered by motors or passive with joints being unpowered. Both active and passive joints can provide readings of the joint angles using encoders. The robot arm 22 can be controlled by an operator and acquire a plurality of images containing an ROI from different angles, within the same plane of imaging. The ROI can be a voxel or volumetric pixel.

FIG. 2 illustrates movement of an ultrasound probe 14 by a robot arm 22 for angle compounding. The ultrasound probe 14 can scan across skin 24 of a patient. An ROI can be imaged for a plurality of frequencies from different angles. These images can be aligned using the position and orientation of the ultrasound probe 14 measured based on the position of the robot arm 33. The dots in FIG. 2 indicate the position of the locations where the ultrasound probe 14 is in contact with the skin 24 of a patient. FIG. 2 illustrates the same ROI being imaged by the ultrasound probe from 9 angles. At each of these 9 angles, ultrasound image data can be obtained for a plurality of different frequencies. The ROI can be imaged at any suitable number of different angles.

The position and orientation of the ultrasound probe 14 can be tracked by the robot arm 22. The accuracy of the position and orientation measurement can ensure that the error introduced in registering the images is relatively small compared to an ultrasound voxel size (e.g., less than ⅓ of the voxel size). Spatial compounding of the images can be achieved by registering the individual images according to the ultrasound probe 14 position and orientation and then averaging the corresponding pixels in the images. Corrections for the distortion of the tissue can be performed. To prevent the powered robotic arm 22 from exerting excessive force to the subject, the pressure that a transducer of the ultrasound probe 14 applies to the subject can be monitored with one or more pressure sensors (e.g., the pressure sensor 15 of FIG. 1) integrated with a head of the ultrasound probe. At the same time, the robot arm 22 can be stopped in response to detecting that the safety current limits in the joint motors are being exceeded.

Although FIG. 2 illustrates 100% overlap in the ROI for the ultrasound probe being in different positions, any suitable principles and advantages disclosed herein can be applied to processing ultrasound images for regions and/or voxels with less than 100% overlap. For example, ultrasound image data corresponding to different angles and partially overlapping regions of an object being imaged can be angle compounded. Even with only partial overlap of a region and/or voxel for ultrasound image data corresponding to different angles (e.g., 4 or 5 different angles), speckle can be significantly reduced by applying combined frequency and angle compounding. Speckle reduction across a full image that corresponds to a plurality of regions and/or voxels can vary based on how much different angle compounded images overlap with each other, which can be similar to how a foveated image can vary in resolution.

In certain instances, a visual display can guide an operator in moving an ultrasound probe. The visual display can be the user interface 12 of FIG. 1, for example. The guidance can direct the operator to increase and/or maximize coverage of the ROI (e.g., as shown in FIG. 2). Guidance in moving an ultrasound probe can be implemented, for example, in a case where a robot arm is a measurement tool that is moved by an operator.

Figure 3A:
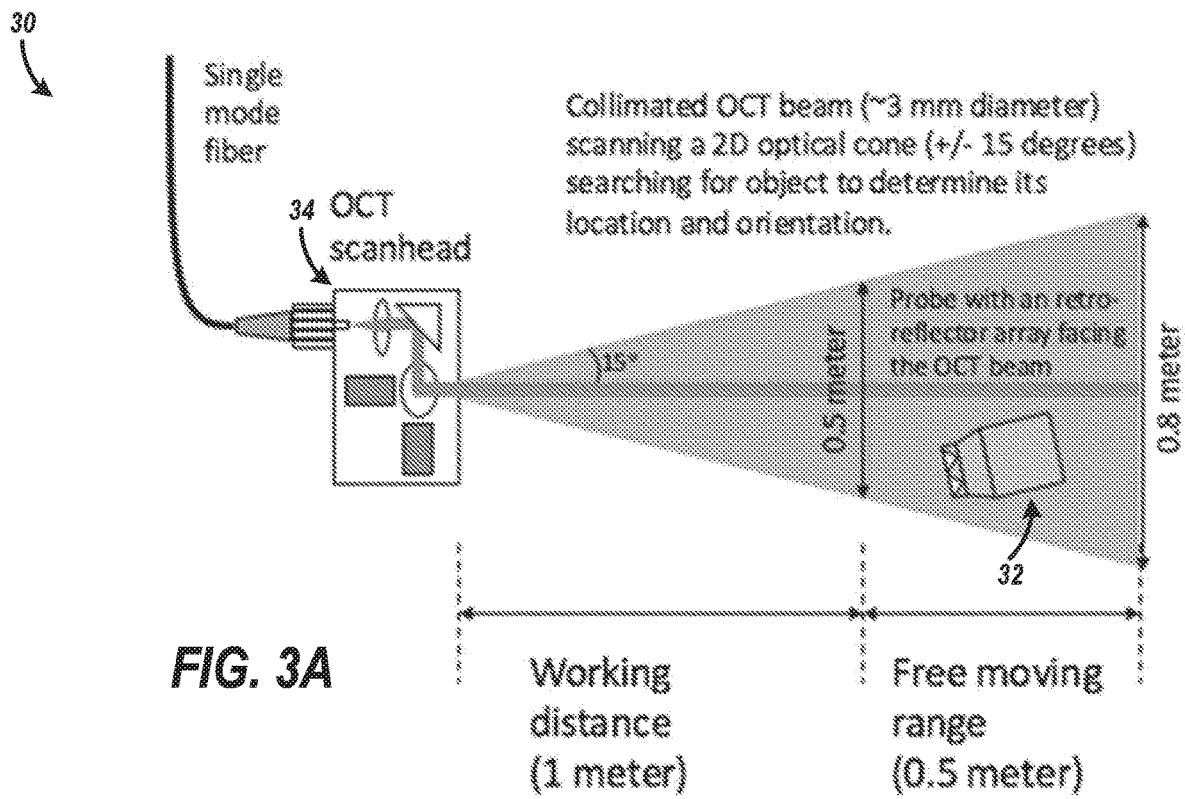
FIG. 3A illustrates an ultrasound system with an optical system for tracking an ultrasound probe according to an embodiment.
Figure 3B:
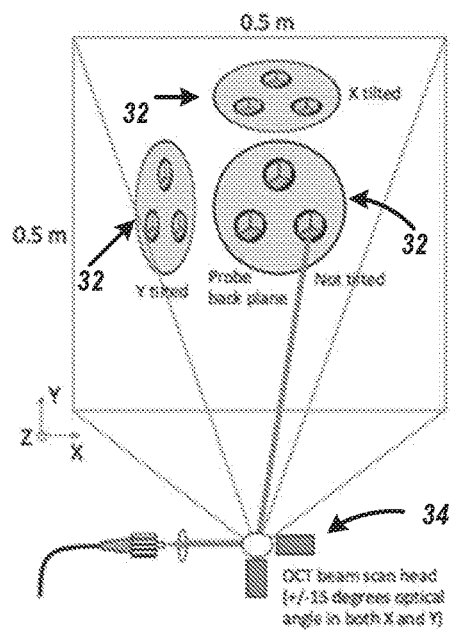
FIG. 3B illustrates the ultrasound probe of the ultrasound system of FIG. 3A y tilted, x tilted, and not tilted.

In another embodiment, the position and orientation of the ultrasound probe can be tracked by an external imaging device that is capable of depth sensing, such as an optical coherence tomography (OCT) imaging system. FIG. 3A illustrates an ultrasound system 30 with an optical system for tracking an ultrasound probe 32 according to an embodiment. As shown in FIG. 3A, a scan head 34 including a collimating lens, a mirror, and a pair of galvo mirrors can control the direction of the OCT laser beam, in a typical range of #15°. At each angle, the frequency of the optical beam can be swept and the power of the interference signal with a reference beam can be recorded. FIG. 3A also includes example distances for a working distance, a free moving range, and a width of the OCT beam at certain points. The depth of a reflector can be determined from the Fourier components of the spectrum. An array of retroreflectors can be attached on the ultrasound probe 32 in FIG. 3A and their positions in the OCT image can determine the position and orientation of the ultrasound probe 32. The position of each retroreflector in the array can be measured to a precision of approximately 300 µm from the centroid of its reflection profile in the OCT image, for example. The precision can exceed the typical ultrasound voxel size of approximately 1 mm at around 5 MHz, and hence should not introduce significant error when angle compounding is performed. The retroreflectors can be tilted to different directions to enhance the range that the ultrasound probe 32 can be tracked. FIG. 3B illustrates the ultrasound probe 32 y-tilted, x-tilted, and not tilted being sensed by the optical system.

In an elastic image registration process, a sensed image can be aligned with a reference image. The sensed image can be distorted to minimize a loss function. The optimization process can be repeated several times until a stop condition is reached.

Figure 4:
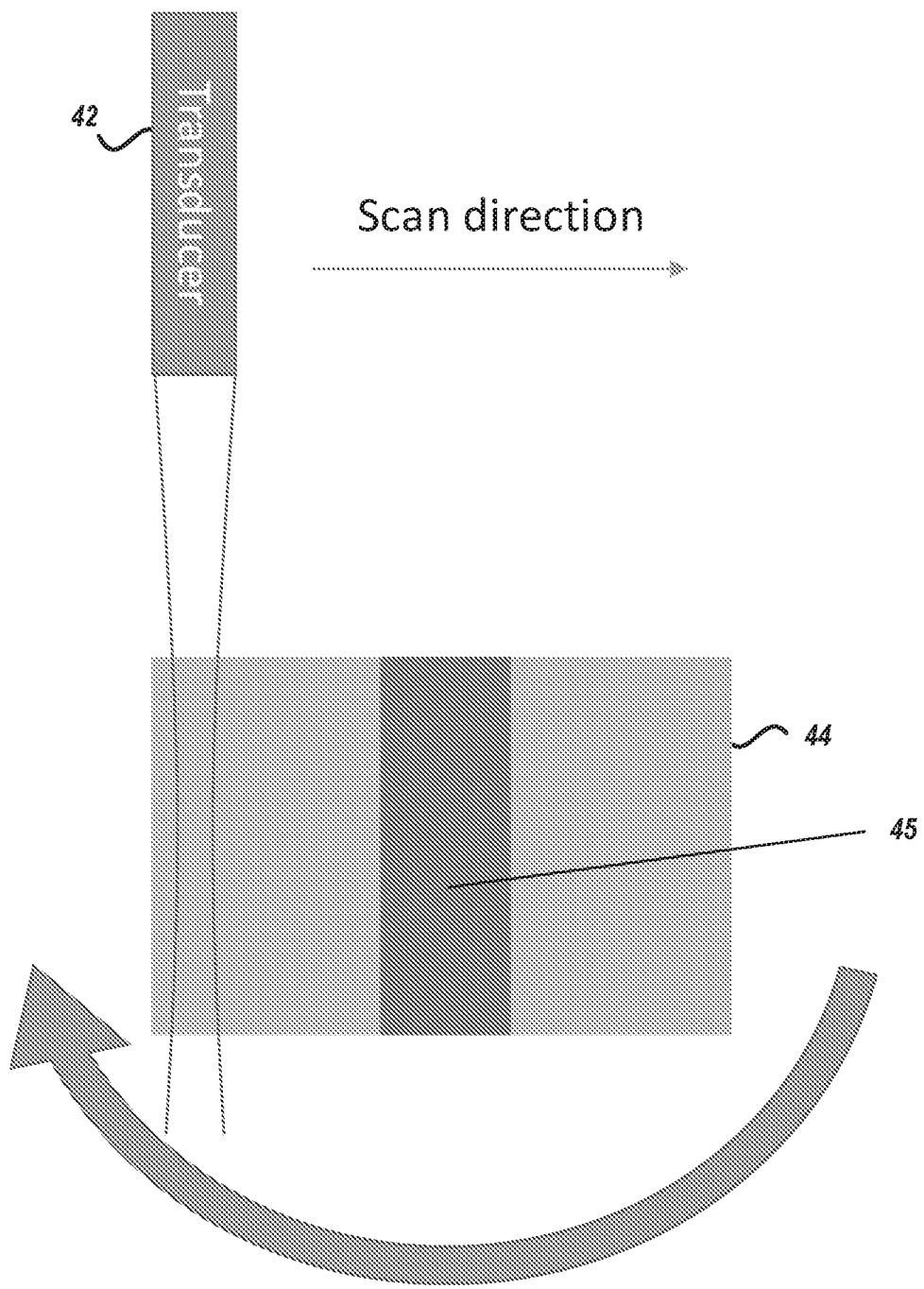
FIG. 4 illustrates a setup of a proof of principle experiment with a single transducer element.

FIG. 4 illustrates a setup of a proof of principle experiment with a single transducer element 42. The transducer element 42 is swept through an agarose phantom 44 with corn starch particles. The corn starch particles can act as point scatters. The agarose phantom 44 has a region 45 with 3 times the corn starch particle density compared to other regions of the agarose phantom 44.

Figure 5:
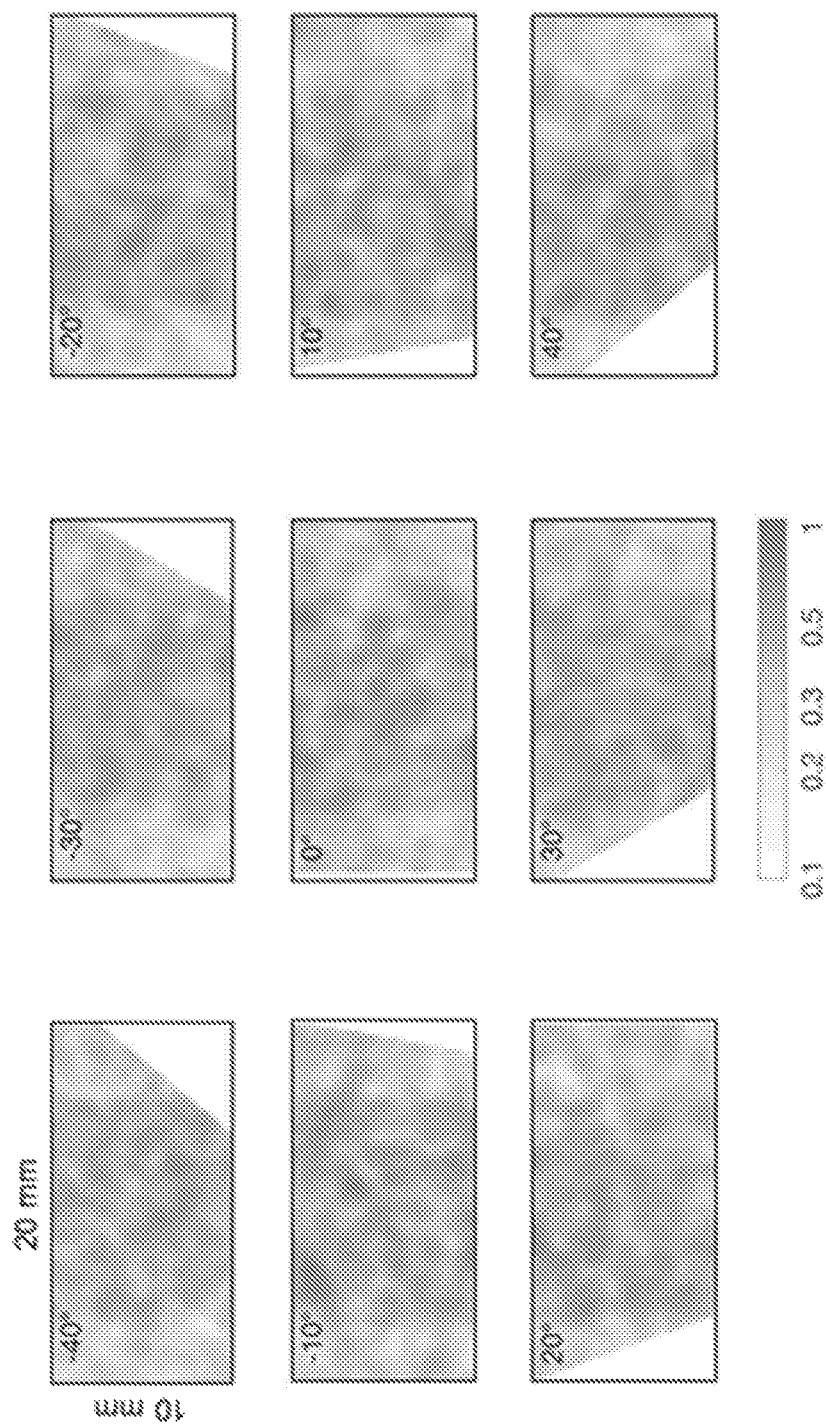
FIG. 5 shows frequency compounded images of an agarose phantom for different angles.

Preliminary data will now be discussed. FIG. 5 shows the frequency compounded images of the agarose phantom 44 from 9 different angles, with 10° spacing between angles. The amplitude of the ultrasound image is plotted by the scale in the bottom middle of FIG. 5. The images are rotated and spatially registered so that they correspond to the same spatial region. Frequency compounding at each angle is performed by transmitting 9 Gaussian pulses centered at 2.4 MHZ, 3.0 MHZ, . . . , 7.2 MHZ, each with a spectral width of $\sigma_f$=0.14 MHz. The width of the pulses gives an axial resolution of 1.4 mm, which is comparable to the transverse resolution of 1.2 mm at 5 MHz. The transverse resolution $\Delta x \approx \lambda/2NA$ is determined by the wavelength $\lambda$ (0.3 mm at 5 MHz) and the numerical aperture of the ultrasound transducer NA=0.12.

Figure 6:
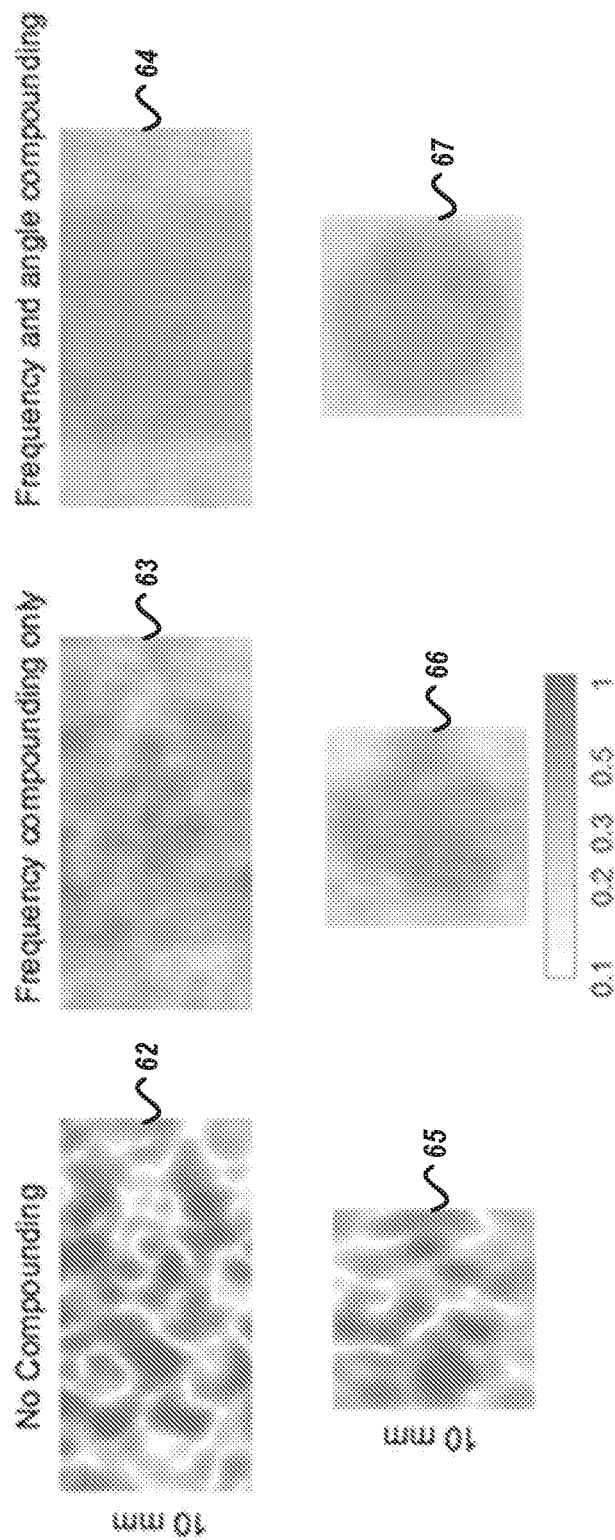
FIG. 6 illustrates images without compounding, with a frequency compounding only, and with combined frequency and angle compounding.

FIG. 6 illustrates images without compounding, with a frequency compounding only, and with combined frequency and angle compounding. The agarose phantom 44 was imaged at a single point (0°) and frequency (4.8 MHz) for the image 62. Images were compounded for 9 frequencies (2.4 MHz, 3.0 MHz, . . . , 7.2 MHz) and a single angle (0°) to generate the image 63. Images were compounded for 9 frequencies (2.4 MHZ, 3.0 MHz, . . . , 7.2 MHZ) and 9 angles (−40°, −30°, . . . , 40°) to generate the image 64.

To quantify speckle, we consider the dimensionless quantity u/o, where u and o are the mean and standard deviation of the speckle amplitude, respectively. For densely and randomly distributed scatterers, µ/σ is equal to a constant of 1.9. The reduction in µ/σ measured inside the center region is 8.8×, significantly larger than that using frequency or angle compounding alone, which reduce speckle by 2.9× and 3.1×, respectively. On the other hand, the measured 8.8× speckle reduction is consistent with the theoretical $\sqrt{MN}$=9× improvement for M=N=9.

In comparison with the experiment, numerical simulation is performed with $4\times10^4$ particles distributed in an area of 10 mm×10 mm. The particle distribution is random except that its density is 3× higher in a circular region with 8 mm diameter. Further increasing the total number of particles does not show any significant effect in the simulated speckle reduction. The speckle images without compounding, with frequency compounding only and with combined frequency and angle compounding are shown in the images 65, 66, and 67, respectively. All experiment and simulated images use the same shading scale shown at the bottom of FIG. 6. The corresponding speckle reductions are 1.0×, 3.5×, and 9.0×, respectively, confirming the multiplicative speckle reduction with frequency and angle.

Figure 7:
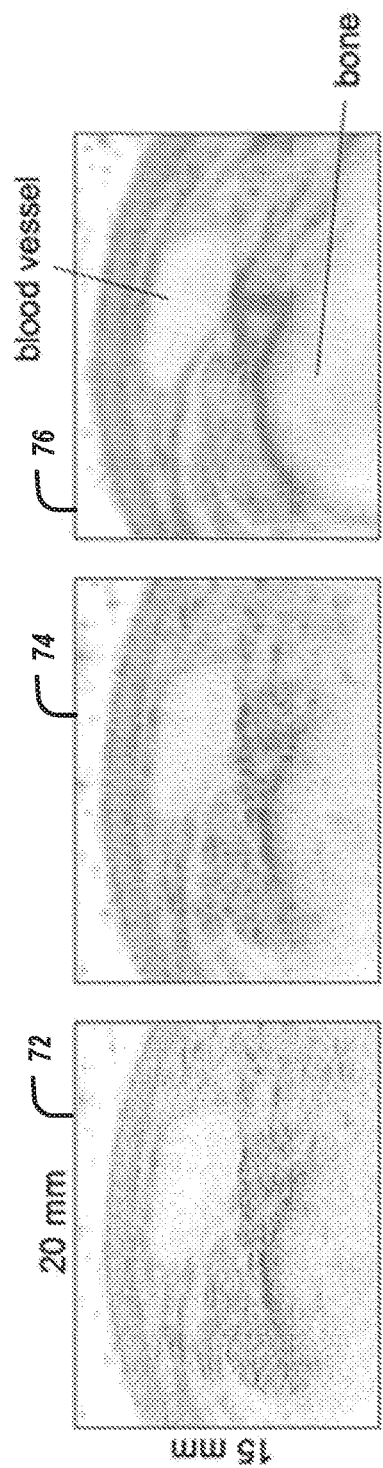
FIG. 7 shows the comparison of images without compounding, with a 9-fold frequency compounding only, and with a 9×9-fold frequency and angle compounding.
Figure 8:
FIG. 8 shows the overlaid false color images taken at two angles before and after the fine adjustment.

A person's forearm was imaged from 9 different angles using a robot arm and a commercial linear array. FIG. 7 shows the comparison of images without compounding, with a 9-fold frequency compounding only, and with a 9×9-fold frequency and angle compounding. A first image 72 of a forearm at a single angle and frequency is shown, a second image 74 of the forearm is compounded at 9 different frequencies for a single angle, and a third image 76 of the forearm is compounded at 9 frequencies for 9 different angles. The frequencies were spaced apart by 0.8 MHz and the angles were spaced apart by 10° to generate the compounded images. The improved clarity in the anatomic features is evident after the coarse alignment considering the movement of the robot arm. Fine adjustment in the image registration is applied for angle compounding. Here the correlation between sections of the adjacent images is calculated as a function of their relative displacement. The displacement that corresponds to maximum correlation is used to correct for the movement in tissue during the image acquisition. FIG. 8 shows the overlaid false color images taken at two angles before and after the fine adjustment. The alignment of the anatomic features is improved by the fine adjustment.

Figure 9:
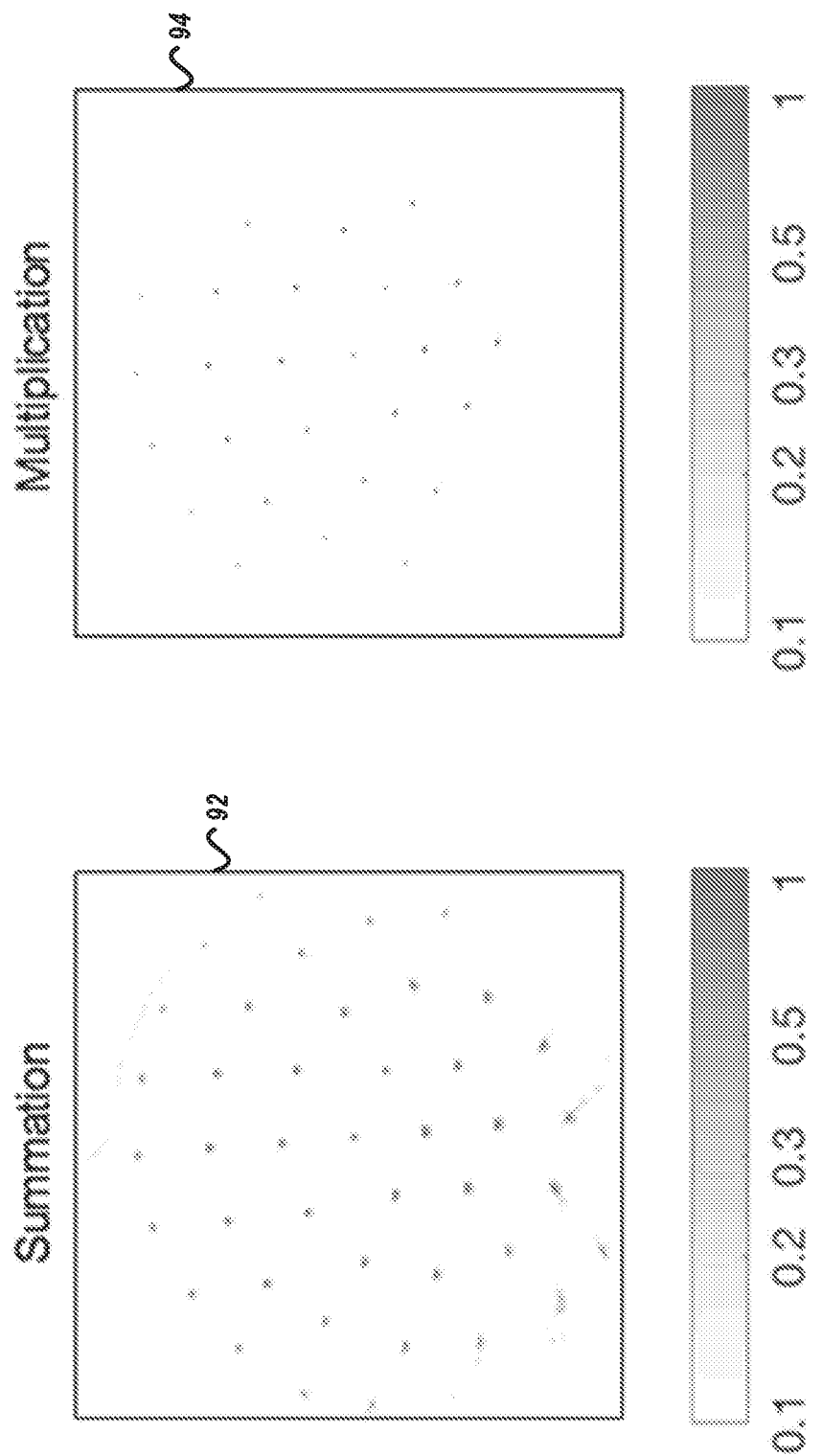
FIG. 9 shows an angle compounded image generating by summing and another angle compound image generated by multiplying.

In certain embodiments, angle compounding can be performed by multiplying individual images, rather than summing. FIG. 9 shows the angle compounded images 92 and 94 of an array of fishing lines. Each bright spot in the images corresponds to one fishing line. To generate the first image 92, individual images corresponding to different angles were summed. The second image 94 was generated by multiplying individual images corresponding to different angles. When the images from different angles are multiplied, the overlapping region of the elongated point spread functions is enhanced, resulting in a 3 to 5 times sharper point spread function.

Figure 10:
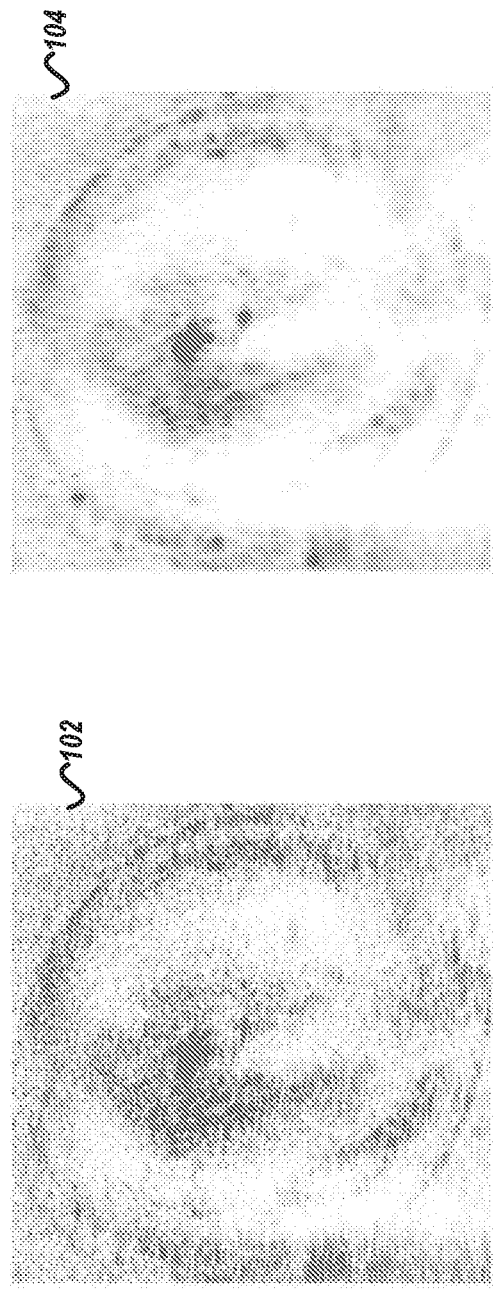
FIG. 10 shows ultrasound images of a chicken heart without compounding, with frequency compounding only, and with combined frequency and angle compounding.
Figure 10:
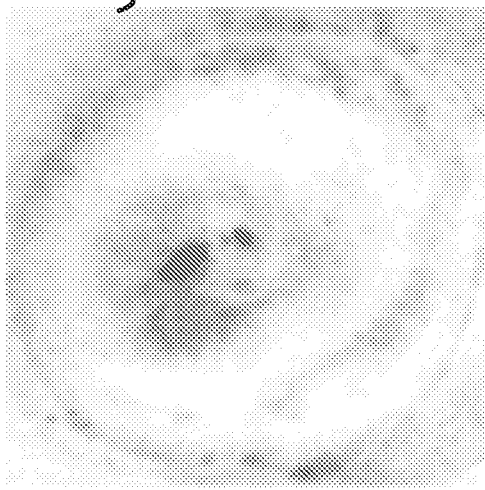

The ultrasound imaging disclosed herein can be applied to a variety of different objects. Combined frequency and angle compounding has shown speckle reduction for ultrasound imaging different tissues. FIG. 10 shows ultrasound images of a chicken heart. The chicken heart images are another example that illustrates that combined frequency and angle compounding can reduce speckle in ultrasound images. A first image 102 of the chicken heart was generated without compounding, a second image 104 of the chicken heart was generated with frequency compounding, and a third image 106 of the chicken heart was generated with combined frequency and angle compounding. These images show that combined frequency and angle compounding can significantly reduce speckle in ultrasound imaging.

In addition to frequency and angle, the wavefront of the ultrasound pulse may be modulated to further reduce speckle. In optical coherence tomography, the modulation of wavefront has been implemented by putting a ground glass in the conjugate plane of the optical focal point. In ultrasound, pulses with different wavefronts can be formed by applying phase delays and amplitude modulations to the signals generated by the individual transmit elements. It can also be implemented at receive, where phase delays and amplitude modulations can be applied to the signal detected by the individual receive elements. Imaging parameters can be varied to obtain different speckle images, including frequency, angle, and the wavefront of sound.

Figure 11:
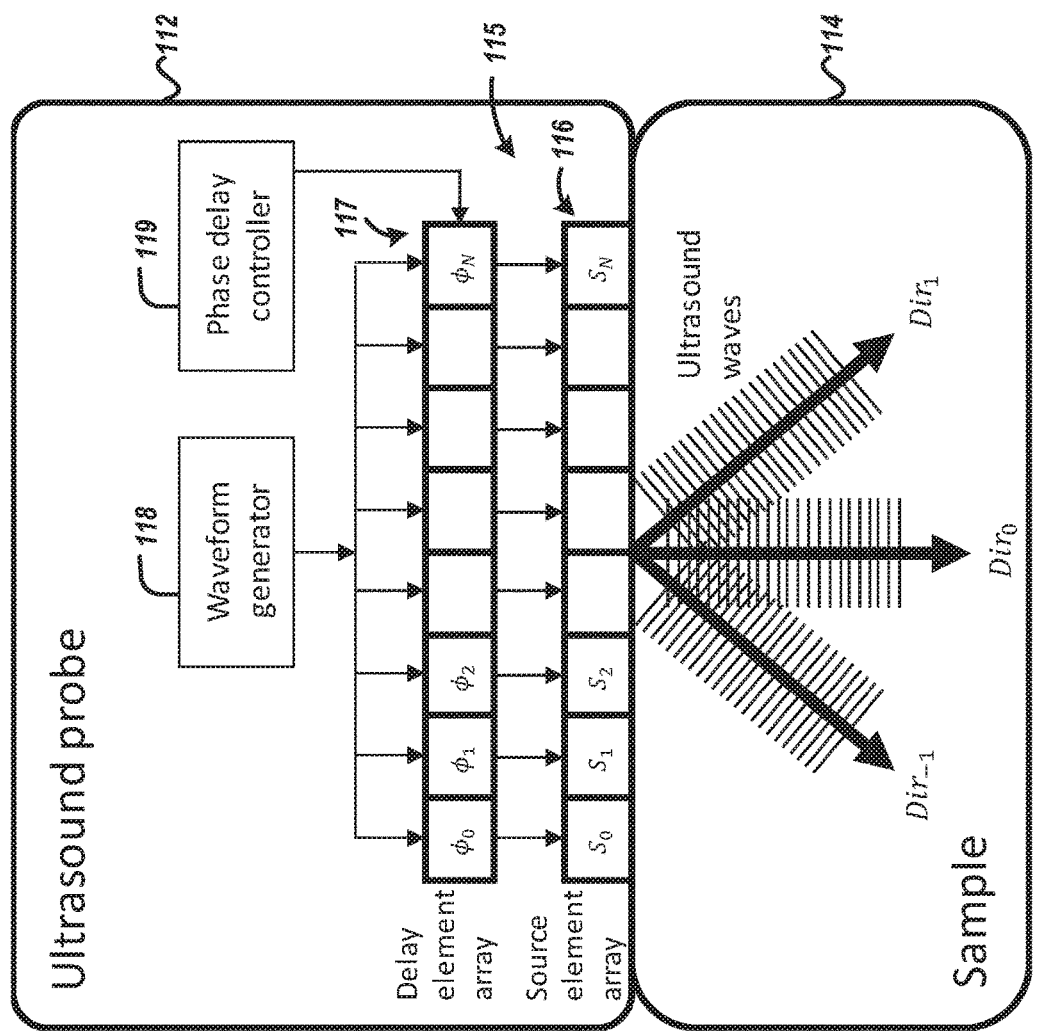
FIG. 11 is a diagram of an ultrasound probe with beam steering to direct ultrasound waves in different directions in a sample according to an embodiment.

FIG. 11 is a diagram of an ultrasound probe 112 with beam steering to direct ultrasound waves in different directions in a sample 114 according to an embodiment. FIG. 11 illustrates an example of ultrasound beam steering for angle compounding for speckle reduction in ultrasound imaging. Ultrasound beams can be steered to measure different angles using a 1-dimensional (1D) phase array 115. This can involve varying the phase delay generated by each source element 116 using delay elements 117. When the source elements 116 are activated at different times, the interference of the sound waves from all the source elements 116 can produce a wavefront tilted at a certain angle that is controllable by the phase delay. Accordingly, in such a system, an imaging angle can be adjusted without changing the contact condition of the ultrasound probe 112 and the sample 114. Ultrasound images from different angles containing an overlapping sample region can be measured and processed to reduce the speckle noise in an ultrasound image.

In an embodiment, an electronic waveform generator 118 generates a pulse shaped waveform that experiences different phase delay do to ØN by a series of delay elements 117 in a delay element array. The amount of phase delay between each of the delay elements 117 is accurately controlled by a phase delay controller 119. A series of ultrasound source elements 116 in a source element array is configured for each source element 116 to receive the phase delayed pulse from one delay element 117 in the delay element array. The source elements 116 can convert the electronic pulses into ultrasound pulses propagating in the sample 114. When the phase delay between adjacent delay elements 117 is 0, all source elements 117 can generate the ultrasound pulses at the same time, producing a wavefront propagating in direction $Dir_0$. When the phase delay is $\Delta\phi$, the effective wavefront of the ultrasound wave propagates direction $Dir_1$, with the angle $\theta$ between $Dir_0$ and $Dir_1$ given by:

$$\frac{\Delta\phi}{2\pi f} = \frac{d\sin(\theta)}{c}$$

In this equation, f is the frequency of the ultrasound pulse, d is the distance between each source element, and c is the speed of sound.

Figure 12:
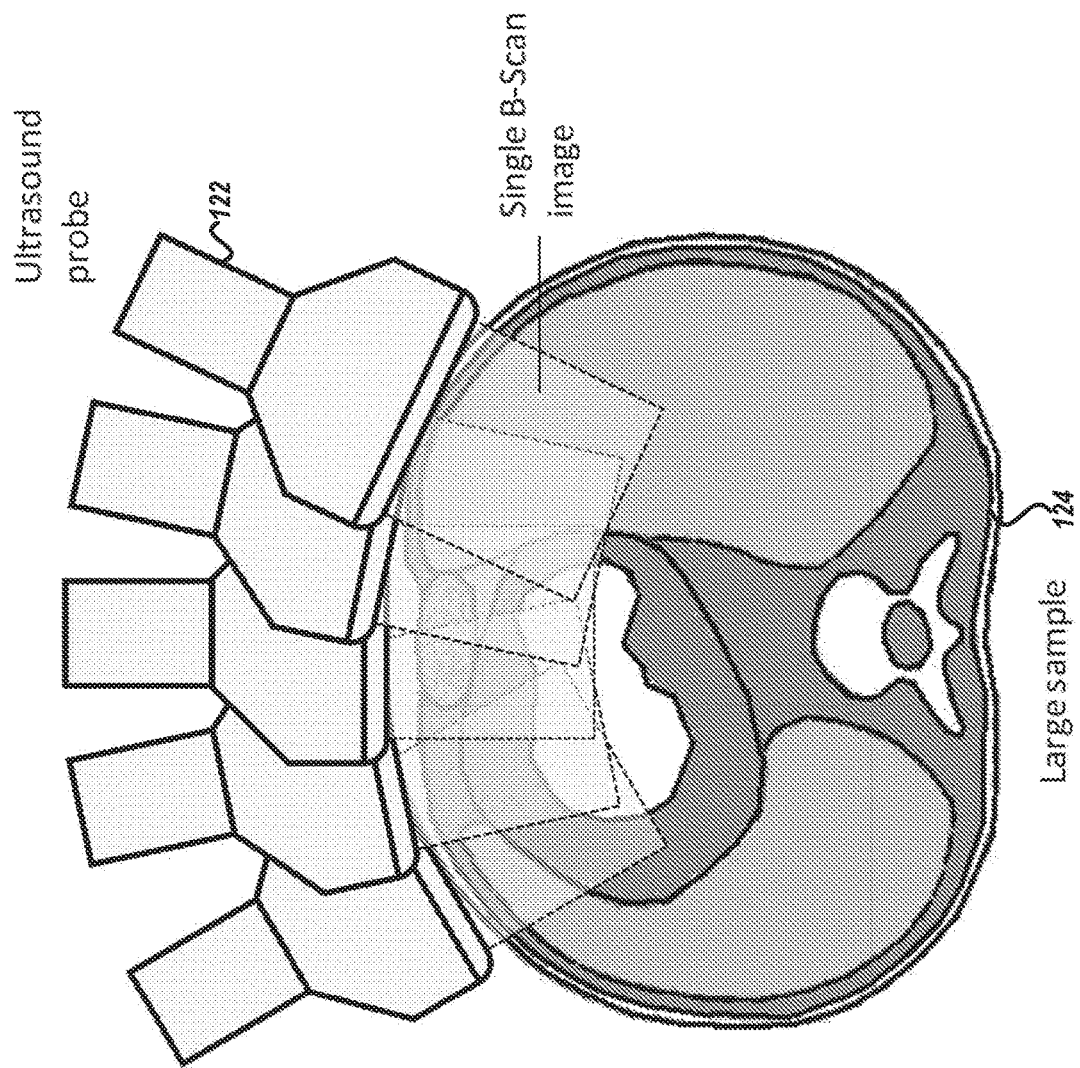
FIG. 12 is a diagram of an ultrasound probe generating a panoramic ultrasound image of a sample with a relatively large field of view, relatively high sensitivity, and reduced speckle according to an embodiment.

FIG. 12 is a diagram of an ultrasound probe 122 generating a panoramic ultrasound image of a sample 124 with a relatively large field of view, relatively high sensitivity, and reduced speckle according to an embodiment. The ultrasound probe 122 is operated by a technician to image the cross-section of a relatively large sample 124 to capture a series of ultrasound images. FIG. 12 shows the ultrasound probe 122 is a variety of different positions as the ultrasound probe 122 is moved by a technician. All ultrasound images are approximately within the same B-Scan plane. There is sufficient overlap in the ultrasound image data covering a same portion of the sample between adjacent images. An image correlation algorithm can process adjacent ultrasound images to calculate the displacement (e.g., translation and rotation) of the ultrasound probe 122 and a point of the image. An elastic distortion compensation algorithm can be applied to correct relatively minor sample distortion during motion of the ultrasound probe 122. A final image is calculated using the displacement and distortion corrected individual images.

This imaging mode can achieve benefits compared to conventional single B-Scan ultrasound images. For example, a larger field-of-view can be achieved when images of multiple sample regions are combined into a final image of the sample. As another example, a higher sensitivity can be achieved when the signals of the sample region captured in multiple images are averaged and displayed in the final image. Reduced speckle noise can be achieved when frequency compounding and spatial compounding methods are used to average the speckle noise in the final image.

FIGS. 13A to 13D illustrate images generated using the ultrasound probe 122 and further processing by the processing circuit according to an embodiment.

Figure 13A:
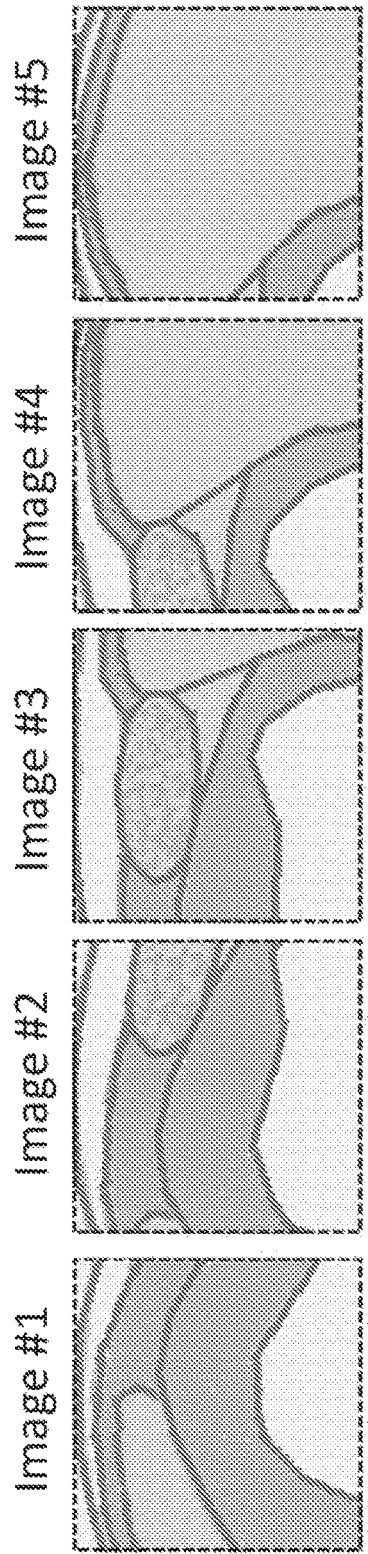

The ultrasound probe 122 can capture a series of images with sufficient coverage of same sample region between adjacent images. FIG. 13A shows 5 images of such a series of images. Frequency compounding can be applied to reduce the speckle in each image.

Figure 13B:
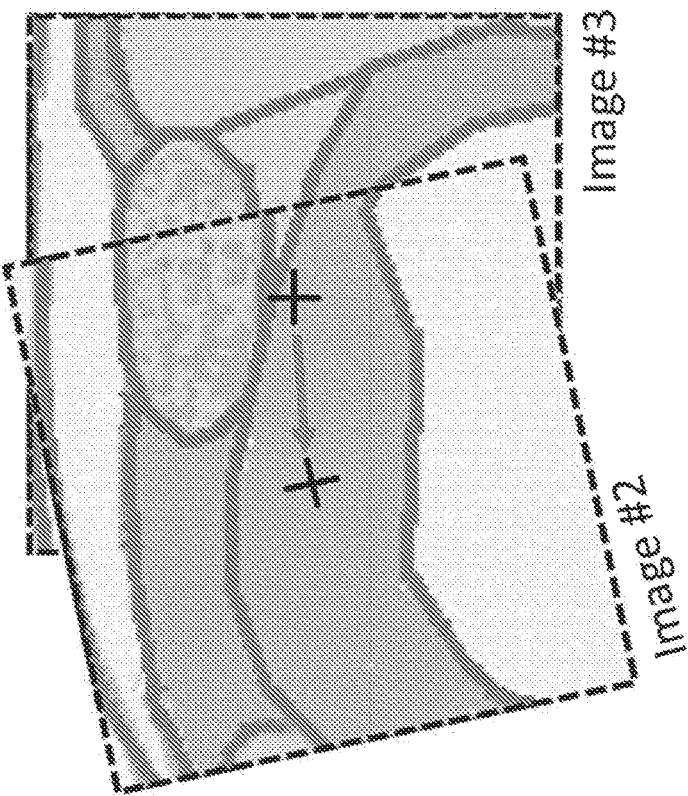

Two adjacent images can be processed to calculate the translation and rotation of the probe (and the center-of-image) using image correlation algorithms. FIG. 13B shows images 2 and 3 from FIG. 13A translated and rotated such that they are aligned with each other. The calculated displacement is marked by an arrow in FIG. 13B. Translating and rotating the images can generate displacement corrected images for later processing.

An elastic sample distortion compensation algorithm can be applied to correct relatively minor sample distortion during motion of the ultrasound probe 122. An image correlation merit function can be maximized when the sample distortion is corrected. This operation can generate sample distortion corrected images for later processing. Example sample distortion corrected images are shown in FIG. 13C.

A final image can be generated based on the both displacement and distortion corrected images. FIG. 13D shows an example of such a final image. A larger field-of-view, higher sensitivity and reduced speckle noise can be achieved in the final image.

Figure 14:
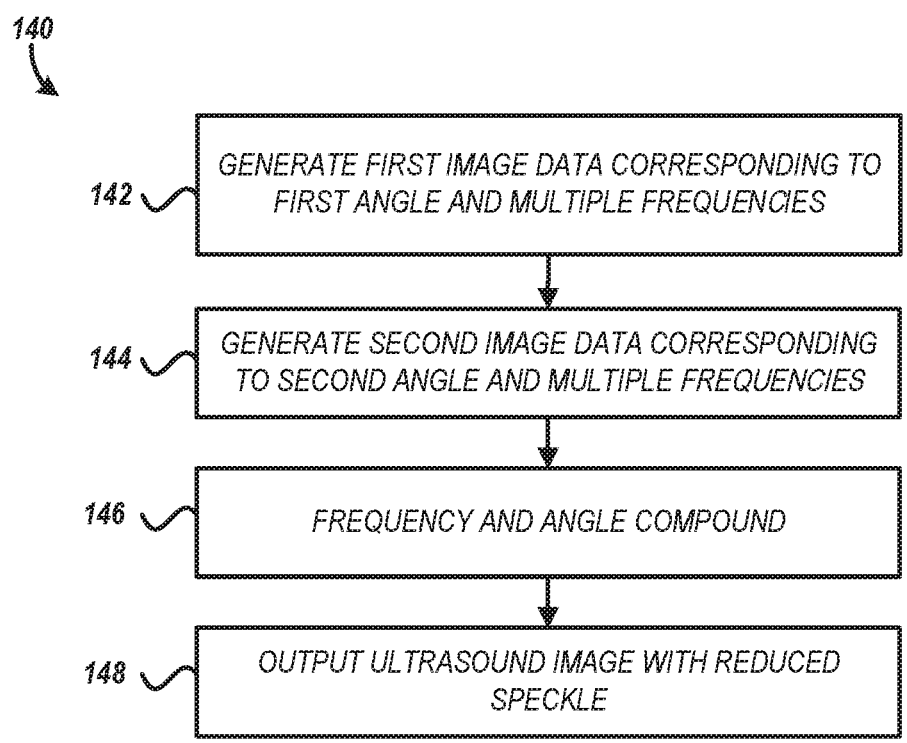
FIG. 14 is a flow diagram of an example method of generating an ultrasound image with reduced speckle according to an embodiment.

FIG. 14 is a flow diagram of an example method 140 of generating an ultrasound image with reduced speckle according to an embodiment. The method 140 can be performed with any suitable ultrasound system disclosed herein. Any suitable principles and advantages of creating an ultrasound image disclosed herein can be implemented in the method 140.

The method 140 includes generating first image data for a voxel of an object corresponding to a first angle and multiple frequencies at block 142. The first image data can be generated with any ultrasound probe disclosed herein and/or with any other suitable ultrasound probe. The ultrasound probe can be used to generate image data for one or more other angles and multiple frequencies for frequency and angle compounding. The method 140 includes generating second image data for the voxel of the object corresponding to a second angle and multiple frequencies at block 144. The first image data and the second image data can correspond to the same voxel imaged from different angles. The multiple ultrasound frequencies of the ultrasound probe for the first image data can be the same as the multiple frequencies of the ultrasound probe for the second image data. In some other instances, one or more of the multiple ultrasound frequencies of the ultrasound probe for the first image data can be different than the multiple frequencies of the ultrasound probe for the second image data. Image data for one or more other angle and multiple frequencies can also be generate by the ultrasound probe.

Any suitable processing circuit can process the image data generated using the ultrasound probe. Such processing includes frequency and angle compounding. The image data can be frequency and angle compounded by at block 146. The first and second image data can be frequency and angle compounded to generate a portion of an ultrasound image that corresponds to an array of voxels that includes the voxel. As discussed herein, frequency and angle compounding can significantly reduce speckle. The frequency compounding can be performed before the angle compounding in certain embodiments. The angle compounding can be performed before the frequency compounding is some other embodiments. Angle and frequency compounding can be performed at least partly concurrently in certain embodiments.

The operations at blocks 142, 144, and 146 can be performed for a plurality of other voxels sequentially and/or at least partly in parallel. This can generate compounded image data for other portions of the ultrasound image.

The ultrasound image is output at block 148 of the method 140. For example, the ultrasound image can be visually presented on a display.

Figure 15:
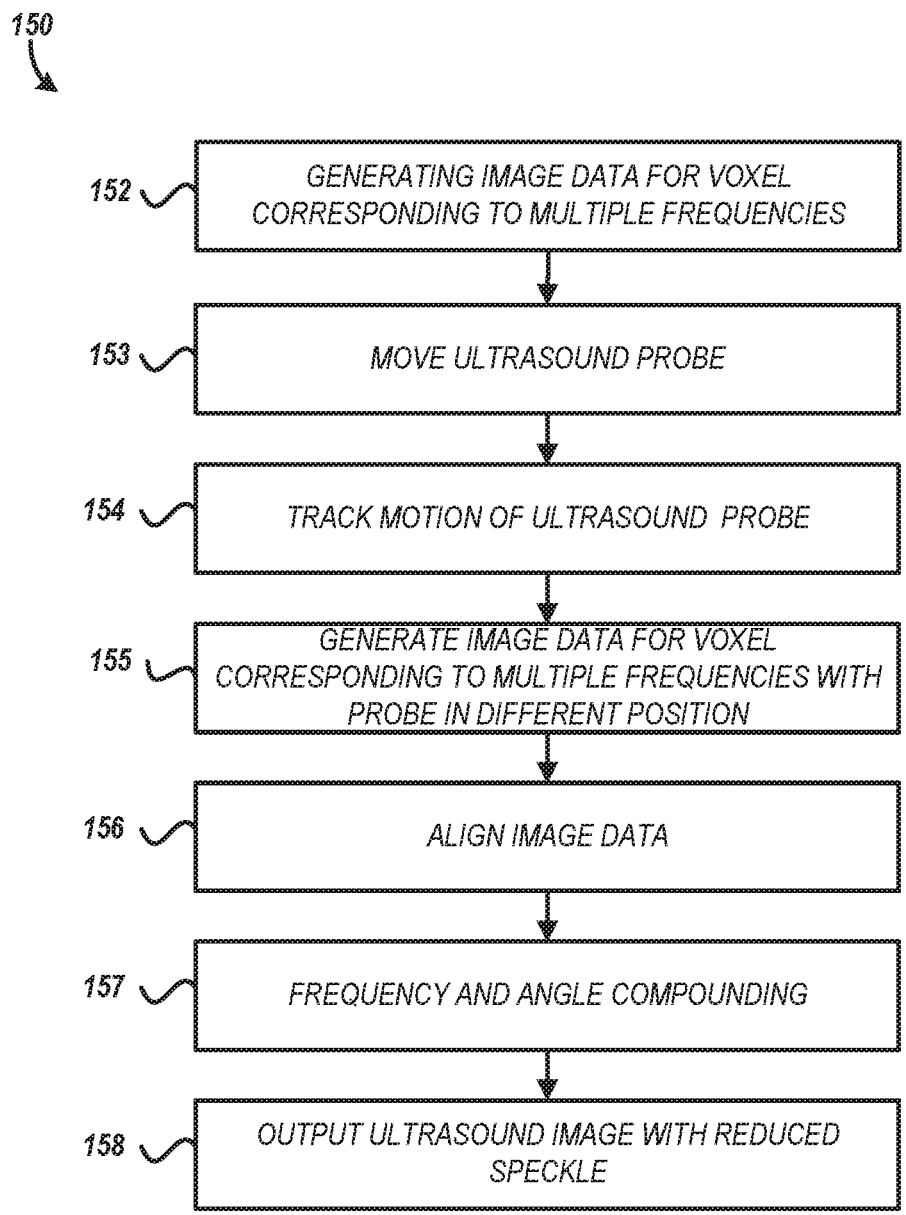
FIG. 15 is a flow diagram of an example method of generating an ultrasound image with reduced speckle according to an embodiment.

FIG. 15 is a flow diagram of an example method 150 of generating an ultrasound image with reduced speckle according to an embodiment. The method 150 can be performed with any suitable ultrasound system disclosed herein. Any suitable principles and advantages of creating an ultrasound image disclosed herein can be implemented in the method 150. The operations of the method 150 and/or any other method disclosed herein can be performed in any suitable order.

The method 150 includes generating first image data for a voxel corresponding to multiple frequencies at block 152. The first image data is generated by an ultrasound probe at a first position. The ultrasound probe is moved at block 153. This can involve at least moving from the ultrasound probe from the first position to a second position. The ultrasound probe can be moved by a technician and/or by a robot arm, for example. The motion of the ultrasound probe can be tracked while the ultrasound probe is moving at block 154. The motion can be tracked in any suitable manner using any suitable sensor and/or sensing system, such as by an inertial sensor, an optical system, a LIDAR system, the like, or any suitable combination thereof. Movement data representative of movement of the ultrasound probe can be generated at block 154. The movement data can be indicative of position and/or orientation of the ultrasound probe. Second image data for the voxel corresponding to multiple frequencies is generated at block 155. The second image data is generated by the ultrasound probe at the second position. The second image data can be generated while the ultrasound probe is moving in certain instances. In some other instances, the second image data can be generated while the ultrasound probe is not moving.

A processing circuit can align the first image data with the second image data at block 156. The alignment can be based on the movement data generated at block 154. The first and second image data can be frequency compounded and angle compounded to generate compounded data for the voxel at block 157. The angle compounding can be performed after the first and second image data are aligned at block 156. The frequency compounding can be performed either before or after the first and second image data are aligned at block 156. By frequency and angle compounding the first and second image data, the voxel can be imaged with reduced speckle.

The operations at blocks 151 to 157 can be performed for a plurality of other voxels sequentially and/or at least partly in parallel. This can generate compounded image data for other portions of the ultrasound image.

At block 158, an ultrasound image is output. The ultrasound image corresponds to any array of voxels of an object being imaged, in which the array of voxels includes the voxel. The ultrasound image can have a resolution that corresponds to substantially a full aperture of the ultrasound probe.

An ultrasound imaging instrument can include a system that uses one or more imaging parameters to form images. One or more of the imaging parameters can be obtained from the scattering coefficient images. Two or more processes for reducing the speckle noise in the scattering coefficient images can be employed. The combination of the noise reducing processes can provide a lower noise than the individual noise reducing process. The speckle noise reduction can improve image clarity.

Any of the signal processing discussed herein can be performed by a processing circuit. The processing circuit includes circuitry configured to perform the signal processing.

While certain embodiments have been described, these embodiments have been presented by way of example only, and are not intended to limit the scope of the disclosure. Indeed, the novel devices, systems, apparatus, and methods described herein may be embodied in a variety of other forms. The principles and advantages of the embodiments can be used for any other suitable devices, systems, apparatuses, and/or methods that could benefit from such principles and advantages. Furthermore, various omissions, substitutions and changes in the form of the methods and systems described herein may be made without departing from the spirit of the disclosure. All possible combinations and sub combinations are intended to fall within the scope of this disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. Any suitable combination of the elements and acts of the various embodiments described above can be combined to provide further embodiments.

Although claims may be presented in single dependency format herein, it is to be understood that any claim depending on any preceding claim of the same type is expressly contemplated except when that is clearly not technically feasible.

What is claimed is:

1. A method of generating an ultrasound image with reduced speckle, the method comprising:
generating, using an ultrasound probe at a first position, first image data for a voxel of an object corresponding to a first angle and first multiple frequencies of the ultrasound probe, wherein the voxel is in a region of interest, the region of interest comprising a plurality of voxels including the voxel, and wherein the region of interest is in a field of view of and at a given radial distance from the ultrasound probe at the first position;
displacing the ultrasound probe in a curve extending from a first position to a second position, wherein at the second position, the region of interest is in the field of view of and at the given radial distance from the ultrasound probe;
generating, using the ultrasound probe at the second position, second image data for the voxel of the object corresponding to a second angle and second multiple frequencies of the ultrasound probe, wherein the first image data and the second image data correspond to the same voxel imaged from different angles;
frequency compounding and angle compounding the first image data and the second image data to generate at least a portion of an ultrasound image that corresponds to the voxel; and
outputting the ultrasound image.

2. The method of claim 1, wherein the ultrasound image uses at least 90% of a full aperture of the ultrasound probe.

3. The method of claim 1, wherein the angle compounding comprises multiplying the first image data and the second image data.

4. The method of claim 1, further comprising aligning the first image data and the second image data, wherein the angle compounding is based on the aligned first and second image data.

5. The method of claim 4, further comprising applying tissue distortion compensation to the aligned first and second image data.

6. The method of claim 1, further comprising:
aligning the first image data and the second image data;
wherein the angle compounding comprises multiplying the aligned first and second image data; and
wherein the ultrasound image uses at least 90% of a full aperture of the ultrasound probe.

7. The method of claim 1, further comprising sensing a pressure applied to the object associated with at least one of the first image data or the second image data.

8. The method of claim 1, further comprising detecting an amount of movement by which the ultrasound probe moves from the first position to the second position using an inertial sensor.

9. The method of claim 1, further comprising detecting an amount of movement by which the ultrasound probe moves from the first position to the second position using an optical coherence tomography system.

10. The method of claim 1, further comprising tracking the movement of the ultrasound probe, wherein a robot arm moves the ultrasound probe from the first position to the second position.

11. The method of claim 1, further comprising detecting an amount of movement by which the ultrasound probe moves from the first position to the second position using an optical system.

12. The method of claim 1, further comprising visually displaying information to guide an operator of the ultrasound probe regarding the movement of the ultrasound probe.

13. The method of claim 1, wherein the ultrasound probe comprises a phased array transducer arranged to transmit a first beam at the first angle to the voxel and to transmit a second beam at the second angle to the voxel.

14. The method of claim 1, further comprising visually displaying the ultrasound image.

15. The method of claim 1, further comprising:
frequency compounding and angle compounding third and fourth image data to generate another portion of the ultrasound image that corresponds to a second voxel, wherein overlap of the third and fourth image data correspond to only a portion of the second voxel being imaged from different angles.

16. The method of claim 1, wherein the first multiple frequencies are the same as the second multiple frequencies.

17. The method of claim 1, wherein displacing the ultrasound probe comprises:
translating the ultrasound probe with respect to the region of interest; and
rotating the ultrasound probe with respect to the region of interest.

18. The method of claim 17, wherein rotating the ultrasound probe comprises rotating the ultrasound probe at least 10 degrees.

19. The method of claim 1, wherein the voxel is centered in the field of view of the ultrasound probe at the first position, and wherein the voxel is centered in the field of view of the ultrasound probe at the second position.

20. The method of claim 1, further comprising:
displacing the ultrasound probe from the first position to one or more intermediate positions that are located between the first position and the second position, wherein the region of interest is in the field of view of the ultrasound probe at each of the one or more intermediate positions,
generating additional image data for the voxel at each of the one or more intermediate positions, and
frequency compounding and angle compounding the first image data, the second image data, and the additional image data to generate at least the portion of the ultrasound image that corresponds to the voxel.

21. The method of claim 20, wherein the region of interest is centered in the field of view of the ultrasound probe at each of the one or more intermediate positions.

22. The method of claim 20, wherein the voxel is centered in the field of view of the ultrasound probe at each of the one or more intermediate positions.

23. The method of claim 19, wherein the one or more intermediate positions comprise seven intermediate positions.

24. The method of claim 1, wherein the region of interest is centered in the field of view of the ultrasound probe at the first position, and wherein the region of interest is centered in the field of view of the ultrasound probe at the second position.

25. The method of claim 1, wherein a difference between the first angle and the second angle is equal to or greater than eighty degrees of arc.

26. The method of claim 1, wherein generating the first image data comprises modulating the wavefront of an ultrasound pulse of the ultrasound probe by applying phase delays and amplitude modulations.

* * * * *

UNITED STATES PATENT AND TRADEMARK OFFICE
CERTIFICATE OF CORRECTION

| | | |
|---|---|---|
| PATENT NO. | : 12,133,771 B2 | Page 1 of 1 |
| APPLICATION NO. | : 17/257251 | |
| DATED | : November 5, 2024 | |
| INVENTOR(S) | : Yilei Li et al. | |

It is certified that error appears in the above-identified patent and that said Letters Patent is hereby corrected as shown below:

In the Specification

Please insert the following heading and paragraph in Column 1, Line 16 of the description, immediately following the first full paragraph:
--STATEMENT REGARDING FEDERALLY SPONSORED RESEARCH OR DEVELOPMENT
This invention was made with Government support under contract GM128089 awarded by the National Institutes of Health. The Government has certain rights in the invention.--

Signed and Sealed this
Fourth Day of March, 2025

Coke Morgan Stewart
*Acting Director of the United States Patent and Trademark Office*